United States Patent
Hood et al.

(10) Patent No.: US 11,285,053 B2
(45) Date of Patent: *Mar. 29, 2022

(54) ABSORBENT ARTICLE WITH AN ABSORBENT CORE HAVING TWO LONGITUDINALLY EXTENDING SIDE REGIONS AND A LONGITUDINALLY EXTENDING CENTRAL REGION BETWEEN SAID SIDE REGIONS AND METHOD FOR MANUFACTURING SAID ABSORBENT ARTICLE

(71) Applicant: ESSITY HYGIENE AND HEALTH AKTIEBOLAG, Gothenburg (SE)

(72) Inventors: Prelo M. Hood, Philadelphia, PA (US); Paul Coomes, Philadelphia, PA (US); Mariela Biber, Newark, DE (US); Peter Kacenak, Hôrka (SK)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 516 days.

This patent is subject to a terminal disclaimer.

(21) Appl. No.: 15/768,638

(22) PCT Filed: Oct. 20, 2015

(86) PCT No.: PCT/SE2015/051114
§ 371 (c)(1),
(2) Date: Apr. 16, 2018

(87) PCT Pub. No.: WO2017/069665
PCT Pub. Date: Apr. 27, 2017

(65) Prior Publication Data
US 2018/0303680 A1 Oct. 25, 2018

(51) Int. Cl.
*A61F 13/47* (2006.01)
*A61F 13/15* (2006.01)
(Continued)

(52) U.S. Cl.
CPC .... *A61F 13/4704* (2013.01); *A61F 13/15626* (2013.01); *A61F 13/533* (2013.01);
(Continued)

(58) Field of Classification Search
CPC combination set(s) only.
See application file for complete search history.

(56) References Cited

U.S. PATENT DOCUMENTS

| 5,451,442 A | 9/1995 | Pieniak et al. |
| 5,722,967 A | 3/1998 | Coles |

(Continued)

FOREIGN PATENT DOCUMENTS

| AU | 2014208105 B2 | 8/2015 |
| CN | 1089129 A | 7/1994 |

(Continued)

OTHER PUBLICATIONS

U.S. Appl. No. 15/768,655, Prelo M. Hood.
(Continued)

*Primary Examiner* — Michele M Kidwell
(74) *Attorney, Agent, or Firm* — Buchanan Ingersoll & Rooney PC

(57) ABSTRACT

An absorbent article has a longitudinal direction, a transverse direction and a thickness direction, and includes a fluid permeable topsheet, a fluid impermeable backsheet and an absorbent core enclosed between the topsheet and the backsheet having, in the longitudinal direction, a front section, a rear section and a crotch section between the front section and the rear section. The absorbent core has two longitudinally extending side regions and a longitudinally extending central region between said side regions. The central region and the side regions are spaced apart in the transversal direction by longitudinally extending channel regions. Furthermore, the width of the central region in the transversal (Continued)

direction is less than the width of each of the side regions in the transversal direction, at least in the front section and the rear section, and the channel regions are of less basis weight than the side regions and the central region.

18 Claims, 6 Drawing Sheets

(51) Int. Cl.
    *A61F 13/533*     (2006.01)
    *A61F 13/532*     (2006.01)
    *A61F 13/535*     (2006.01)

(52) U.S. Cl.
    CPC ........... *A61F 13/532* (2013.01); *A61F 13/535* (2013.01); *A61F 2013/4708* (2013.01)

(56) References Cited

U.S. PATENT DOCUMENTS

| | | | |
|---|---|---|---|
| 6,160,197 | A | 12/2000 | Lassen et al. |
| 6,169,223 | B1 | 1/2001 | Mahr |
| 8,394,316 | B2 | 3/2013 | Alkmin et al. |
| 2002/0123732 | A1* | 9/2002 | Koyama ........... A61F 13/49017 604/385.24 |
| 2004/0044320 | A1 | 3/2004 | Kainth |
| 2004/0087928 | A1 | 5/2004 | Ducker |
| 2004/0267220 | A1 | 12/2004 | Hull et al. |
| 2005/0085783 | A1* | 4/2005 | Komatsu ............. A61F 13/4704 604/385.04 |
| 2007/0078422 | A1 | 4/2007 | Glaug et al. |
| 2007/0299416 | A1* | 12/2007 | Noda ................ A61F 13/15658 604/367 |
| 2010/0036348 | A1 | 2/2010 | De Carvalho et al. |
| 2011/0015602 | A1 | 1/2011 | Schmidt et al. |
| 2011/0130737 | A1* | 6/2011 | Sagisaka ............... A61F 13/533 604/380 |
| 2011/0152813 | A1 | 6/2011 | Ellingson |
| 2013/0289509 | A1 | 10/2013 | Mukai et al. |
| 2015/0359687 | A1 | 12/2015 | Goda et al. |
| 2017/0233909 | A1 | 8/2017 | Wright |
| 2018/0311081 | A1 | 11/2018 | Hood et al. |

FOREIGN PATENT DOCUMENTS

| | | |
|---|---|---|
| CN | 1121432 A | 5/1996 |
| CN | 1609322 A | 4/2005 |
| CN | 102440870 A | 5/2012 |
| CN | 103237532 A | 8/2013 |
| CN | 103269669 A | 8/2013 |
| EP | 0589102 A1 | 3/1994 |
| EP | 2417952 A1 | 2/2012 |
| EP | 2656826 A1 | 10/2013 |
| JP | H08-501473 A | 2/1996 |
| JP | 2006-116036 A | 5/2006 |
| JP | 2006-521166 A | 9/2006 |
| JP | 2010-273842 A | 12/2010 |
| RU | 2290154-02 | 12/2006 |
| RU | 2560916 C2 | 8/2015 |
| TW | 201529055 A | 8/2015 |
| WO | WO-94/06386 A1 | 3/1994 |
| WO | WO-2004/084784 A1 | 10/2004 |
| WO | WO-2006/068549 A1 | 6/2006 |
| WO | WO-2012/086487 A1 | 6/2012 |
| WO | WO-2014/112590 A1 | 7/2014 |
| WO | WO-2015/087680 A1 | 6/2015 |

OTHER PUBLICATIONS

International Preliminary Report on Patentability issued in International application No. PCT/SE2015/051115, dated Jul. 2, 2018.
Examination Report No. 1 issued in Australian patent application No. 2015412559, dated Jul. 18, 2018.
Japanese Office Action issued in Japanese patent application No. 2018-520509, dated Jun. 1, 2020.
Russian Office Action issued in Russian patent application No. 2018118169 (7 pages) and its English-language translation thereof (6 pages), dated Feb. 19, 2019.
English-language translation of Brazilian Search Report and Written Opinion issued in Brazilian patent application No. BR112018007930-8, dated Mar. 14, 2020.
English-language translation of Brazilian Search Report and Written Opinion issued in Brazilian patent application No. BR112018007940-5, dated Mar. 14, 2020.
Colombian Office Action Oficion No. 1132 dated Jan. 22, 2020 issued in Colombian patent application No. NC2018/0005006 (11 pages) and its English-language translation thereof (7 pages).
Russian Office Action issued in Russian patent application No. 2018117497, dated Feb. 19, 2019.
Extended European search report issued in European patent application No. 15906801.4, dated Mar. 8, 2019.
Notice of acceptance for patent application issued in Australian patent application No. 2015412560, dated Feb. 28, 2019.
Examination report No. 1 issued in Australian patent application No. 2015412560, dated Jul. 10, 2018.
First Chinese Office Action issued in Chinese patent application No. 201580085419.4, dated May 12, 2020.
Japanese Office Action issued in Japanese patent application No. 2018-520508, dated Jun. 8, 2020.
First Chinese Office Action issued in Chinese patent application No. 201580085003.2, dated May 27, 2020.
Colombian Office Action Oficio No. 4887 dated Jun. 18, 2019 issued in Colombian patent application No. NC2018/0005006 (10 pages) and its English-language translation thereof (6 pages).
Colombian Office Action Oficio No. 4950 dated Jun. 19, 2019 issued in Colombian patent application No. NC2018/0004335 (16 pages) and its English-language translation thereof (7 pages).
Japanese Office Action issued in Japanese patent application No. 2018-520508, dated Aug. 26, 2019.
Japanese Office Action issued in Japanese patent application No. 2018-520509, dated Aug. 26, 2019.
Office Action issued in corresponding Chinese Patent Application No. 201580085419.4, dated Jan. 7, 2021, with English Translation (23 pages).
Office Action (Decision of Rejection) dated Apr. 6, 2021, by the Chinese Patent Office in corresponding Chinese Patent Application No. 201580085419.4, and an English Translation of the Office Action. (25 pages).
Office Action issued in corresponding U.S. Appl. No. 15/768,655, dated Apr. 6, 2021, (22 pages).
Office Action (Decision of Rejection) dated May 11, 2021, by the Chinese Patent Office in corresponding Chinese Patent Application No. 201580085003.2, and an English Translation of the Office Action. (12 pages).
Office Action (Second Office Action) dated Dec. 4, 2020, by the Chinese Patent Office in corresponding Chinese Patent Application No. 201580085003.2, and an English Translation of the Office Action (12 pages).
Office Action (Restriction) dated Jun. 25, 2020, by the U.S. Patent and Trademark Office in co-pending U.S. Appl. No. 15/768,655.
Office Action (Rejection) dated Nov. 27, 2020, by the U.S. Patent and Trademark Office in co-pending U.S. Appl. No. 15/768,655.
Office Action (Advisory Action) dated May 4, 2021, by the U.S. Patent and Trademark Office in co-pending U.S. Appl. No. 15/768,655.
Supplemental Notice of Allowability dated Jul. 21, 2021, by the U.S. Patent and Trademark Office in co-pending U.S. Appl. No. 15/768,655.

* cited by examiner

ABSORBENT ARTICLE WITH AN ABSORBENT CORE HAVING TWO LONGITUDINALLY EXTENDING SIDE REGIONS AND A LONGITUDINALLY EXTENDING CENTRAL REGION BETWEEN SAID SIDE REGIONS AND METHOD FOR MANUFACTURING SAID ABSORBENT ARTICLE

CROSS-REFERENCE TO PRIOR APPLICATION

This application is a § 371 National Stage Application of PCT International Application No. PCT/SE2015/051114 filed Oct. 20, 2015, which is incorporated herein in its entirety.

TECHNICAL FIELD

The disclosure relates to an absorbent article having a longitudinal direction, a transverse direction and a thickness direction, and including a fluid permeable topsheet, a fluid impermeable backsheet and an absorbent core enclosed between the topsheet and the backsheet. The absorbent core has, in the longitudinal direction, a front section, a rear section and a crotch section between the front section and the rear section. The absorbent core has two longitudinally extending side regions and a longitudinally extending central region between said side regions. Also, the central region and the side regions are spaced apart in the transversal direction by longitudinally extending channel regions.

The disclosure also relates to an absorbent core for use in an absorbent article and having two longitudinally extending side regions and a longitudinally extending central region between said side regions, the central region and the side regions being spaced apart in a transversal direction by longitudinally extending channel regions.

The disclosure also relates to a method for manufacturing an absorbent core for use in an absorbent article having a longitudinal direction, a transverse direction and a thickness direction. The method includes: providing a fluid permeable topsheet; providing a fluid impermeable backsheet; forming, in an absorbent core, longitudinally extending channel regions, thereby defining two longitudinally extending side regions and a longitudinally extending central region between said side regions, the central region and the side regions being spaced apart in the transversal direction by said channel regions; and enclosing the absorbent core between the topsheet and the backsheet.

BACKGROUND

Absorbent articles, for example in the form of incontinence liners, baby diapers and sanitary napkins, are well known. The general purpose of such absorbent articles is to absorb, distribute and store various types of body exudates, while providing a high level of comfort and sense of dryness to the wearer during use of the absorbent article. Also, the absorbent articles prevent the wearer from getting the clothes soiled by such body exudates.

In particular, it can be noted that absorbent articles in the form of incontinence liners are used to protect a wearer against light urine leakage. Such leakage may occur as a result of, for example, pregnancy or childbirth, or during physical efforts such as running or even laughing, sneezing or coughing. For this reason, it is known to use incontinence liners which are designed with an absorption capacity which is sufficient in order to absorb the fluid that is expected to be released into the absorbent article when it is worn.

As regards incontinence liners, there exist certain requirements for such type of products. Initially, it should be noted that an incontinence liner should be designed so as to be worn inside a user's ordinary underwear and to provide protection against light urine leakage. For this reason, an incontinence liner of known type is shaped to provide an optimal fit to the user's undergarment and body and also to absorb leaks of urine during use. To this end, the liner includes a core of absorbent material arranged along a longitudinal axis of the product. Also, the liner normally includes a soft topsheet in order to give the wearer a feeling of freshness and dryness. Furthermore, an incontinence liner should be relatively thin and should be designed with a discreet shape so that it is generally not visible through the wearer's clothes during use. Finally, a liner is normally provided with suitable adhesive means, allowing it to be attached to the wearer's underwear.

In particular, it is noted that an incontinence liner should provide softness, pliability and comfort in addition to absorption of urine.

The patent document US 2007/078422 discloses an absorbent article in the form of a diaper which includes a topsheet and a backsheet which enclose an absorbent core. The absorbent core includes two longitudinally extending gaps extending through the thickness of the core and together defining a longitudinally extending central region between the gaps and two longitudinally extending side regions outside the gaps. Consequently, the central region and the side regions are spaced apart in the transversal direction of the absorbent article by longitudinally gaps extending along the core. The purpose of the article according to US 2007/078422 is to provide an absorbent article which is configured so as to provide a controlled deformation of the article during use.

Although the article disclosed in US 2007/078422 is suitable to be used as a diaper and can provide a controlled deformation during use, there is a need for further improvements. In particular, there is a need for improving the pliability of an incontinence liner, which is a particular type of absorbent article.

SUMMARY

There is provided an absorbent article which in particular, but not exclusively, is intended to be used as an incontinence liner and in which properties relating to pliability of the article and the ability to conform to the wearer's anatomy during use are improved in relation to previously known absorbent articles.

As used herein, the term "pliability" means that the liner is designed so that it is easily bent and shaped so as to follow the anatomy of the wearer during use. In particular, the liner is designed so that it bends along its longitudinal direction so as to offer optimal function and fit.

This can be obtained by an absorbent article which has a longitudinal direction, a transverse direction and a thickness direction, and includes a fluid permeable topsheet, a fluid impermeable backsheet and an absorbent core enclosed between the topsheet and the backsheet. The absorbent core has, in the longitudinal direction, a front section, a rear section and a crotch section between the front section and the rear section. Furthermore, the absorbent core has two longitudinally extending side regions and a longitudinally extending central region between said side regions. Also, the central region and the side regions are spaced apart in the transversal direction by longitudinally extending channel regions. Furthermore, the width of the central region in the transversal direction is less than the width of each of the side regions in the transversal direction, at least in the rear section and the front section, and the channel regions are of less basis weight than the side regions and the central region.

As mentioned, the absorbent article as described herein provides a high degree of pliability due to the fact that the absorbent core is designed with channel regions which according to an embodiment are constituted by light basis weight areas having a lower basis weight, i.e. less absorbent material per square area (gsm), than the remaining parts of the absorbent core.

The article will present a high degree of pliability along the direction of the channel regions and a high degree of conformity to the anatomy of the wearer. This is an advantage as regards the comfort and the function of the absorbent article.

The absorbent article has an elongate and generally rectangular shape including a front section, a rear section and a crotch section between the front section and the rear section. The word "generally," as used herein, means that, for instance, the corners of the absorbent article may be rounded. The width of the central region in the transversal direction is less than the width of each of the side regions in the transversal direction, at least in the rear section and the front section. However, the rounded rear end corners and the rounded front end corners are not included in the rear section and the front section.

According to one embodiment, the channel regions with the light basis weight areas are of generally the same thickness as the side regions of the core and the central region. Since the channel regions with the light basis weight areas are of generally the same thickness as the side regions of the core and the central region, the channel regions have also less density than the side regions and the central region. The density is measured with an applied pressure of 0.5 kPa.

According to one embodiment, the ratio of the basis weight between the channel regions and the remaining parts of the absorbent core is at least 2:3, or at least 2:5 or at least 1:2. By remaining parts are meant the side regions and the central region.

According to one embodiment, the ratio of the basis weight between the channel regions and the remaining parts of the absorbent core is between 1:3 to 2:3.

According to a further embodiment, the ratio of the basis weight between the channel regions and the remaining parts of the absorbent core is approximately 1:2.

According to one embodiment, the basis weight of the side regions and the central region is 250-600 gsm or 250-450 gsm.

According to an embodiment, the article has a single absorbent core. By having a single absorbent core, a thin, compact absorbent product which is comfortable and discreet for the wearer is provided.

The central region may, in the crotch section, have a width that is less than ⅖ of the total width of the absorbent core in the crotch section, or less than ⅓ of the total width of the absorbent core in the crotch section, or less than ¼ of the total width of the absorbent core in the crotch section.

According to an embodiment, the article is an incontinence protector, for example, an incontinence liner.

Furthermore, according to an embodiment, the absorbent article includes an acquisition layer generally covering said absorbent core. Such a layer is particularly suitable for use in an incontinence article, since a rapid inlet and distribution of fluid is obtained. This means that the acquisition layer is advantageous in situations involving a discharge of a relatively high volume of fluid in a relatively short time. According to an embodiment, the basis weight of the acquisition layer is 30 to 60 gsm, or 40 to 50 gsm. According to an embodiment, the acquisition layer is a fiber based layer, which for example is a through air bonded nonwoven.

According to one embodiment, the acquisition layer consists essentially of non-absorbent fibers, such as for example thermoplastic polymeric fibers selected from polyolefines, polyesters, polyamides, and blends and combinations thereof.

According to an embodiment, the topsheet is also a nonwoven, for example, spunbond nonwoven, carded thermobonded nonwoven, carded through air bonded nonwoven, or spunlace nonwoven.

According to an embodiment, the width of the central region in the transversal direction is less than the width of each of the side regions in the transversal direction also in the crotch section. The width of the central region in the transversal direction may be less than the width of each of the side regions along the entire length of the absorbent core except for the front and rear end rounded end corners.

According to another embodiment, the width of the central region in the transversal direction is less than the width of each of the side regions in the transversal direction at least in the crotch section.

According to an embodiment, the absorbent core includes superabsorbent material which is generally equally distributed along the absorbent core. More precisely, the amount of said superabsorbent material in said absorbent core is within the interval 25-55%, or 35-50%, of the total weight of the absorbent core.

Furthermore, according to an embodiment, the channel regions are generally parallel and straight along the longitudinal direction of the absorbent article. This leads to optimal properties regarding the pliability of the article.

According to one embodiment, the width of each side regions is at least the same as the width of the central region at its most narrow region. According to a further embodiment, the width of each side regions is greater than the width of the central region at its most narrow region.

According to an embodiment, the absorbent article includes two channel regions, wherein the width of each channel region is approximately 2-3 millimeters.

According to one embodiment, the width of the central region is 6-12 mm, 7-10 mm, or 8-9 mm.

According to a further embodiment, the width of each channel region is less than 0.4 times the width of a corresponding side region. The width of each channel region may be less than 0.1 times the width of the absorbent core at its most narrow region.

According to one embodiment, the channel regions extend along the entire length of the absorbent core.

According to one embodiment, the material of the absorbent core is of the same type both in the channel regions and the remaining parts of the absorbent core, but there is however less material per square area in the channel regions as compared to the other areas of the core. The absorbent core may be a single continuous layer.

Furthermore, in an aspect, an absorbent core for use in an absorbent article has two longitudinally extending side regions and a longitudinally extending central region between said side regions, the central region and the side regions being spaced apart in a transversal direction by longitudinally extending channel regions. Said absorbent core also has, in the longitudinal direction, a front section, a rear section and a crotch section between the front section and the rear section. Furthermore, the width of the central region in the transversal direction is less than the width of each of the side regions in the transversal direction, at least in the front section and the rear section. Also, the channel regions are of less basis weight than the side regions and the central region.

In an aspect, a method for manufacturing an absorbent core for use in an absorbent article has a longitudinal direction, a transverse direction and a thickness direction. The method includes: providing a fluid permeable topsheet; providing a fluid impermeable backsheet; forming, in an absorbent core, longitudinally extending channel regions, thereby defining two longitudinally extending side regions and a longitudinally extending central region between said side regions, the central region and the side regions being spaced apart in the transversal direction by said channel regions; and enclosing the absorbent core between the topsheet and the backsheet, wherein said absorbent core has, in the longitudinal direction, a front section, a rear section and a crotch section between the front section and the rear section. Furthermore, the method includes: forming said central region with a width in the transversal direction which is less than the width of each of the side regions in the transversal direction, at least in the front section and the rear section; and forming said channel regions with less basis weight than the side regions and the central region.

BRIEF DESCRIPTION OF THE DRAWINGS

Embodiments of the invention will be described in greater detail below with reference to the figures shown in the appended drawings.

DESCRIPTION OF PARTICULAR EMBODIMENTS

Different aspects of the present disclosure will be described more fully hereinafter with reference to the enclosed drawings. The embodiments disclosed herein can, however, be realized in many different forms and should not be construed as being limited to the aspects set forth herein.

Figure 1:
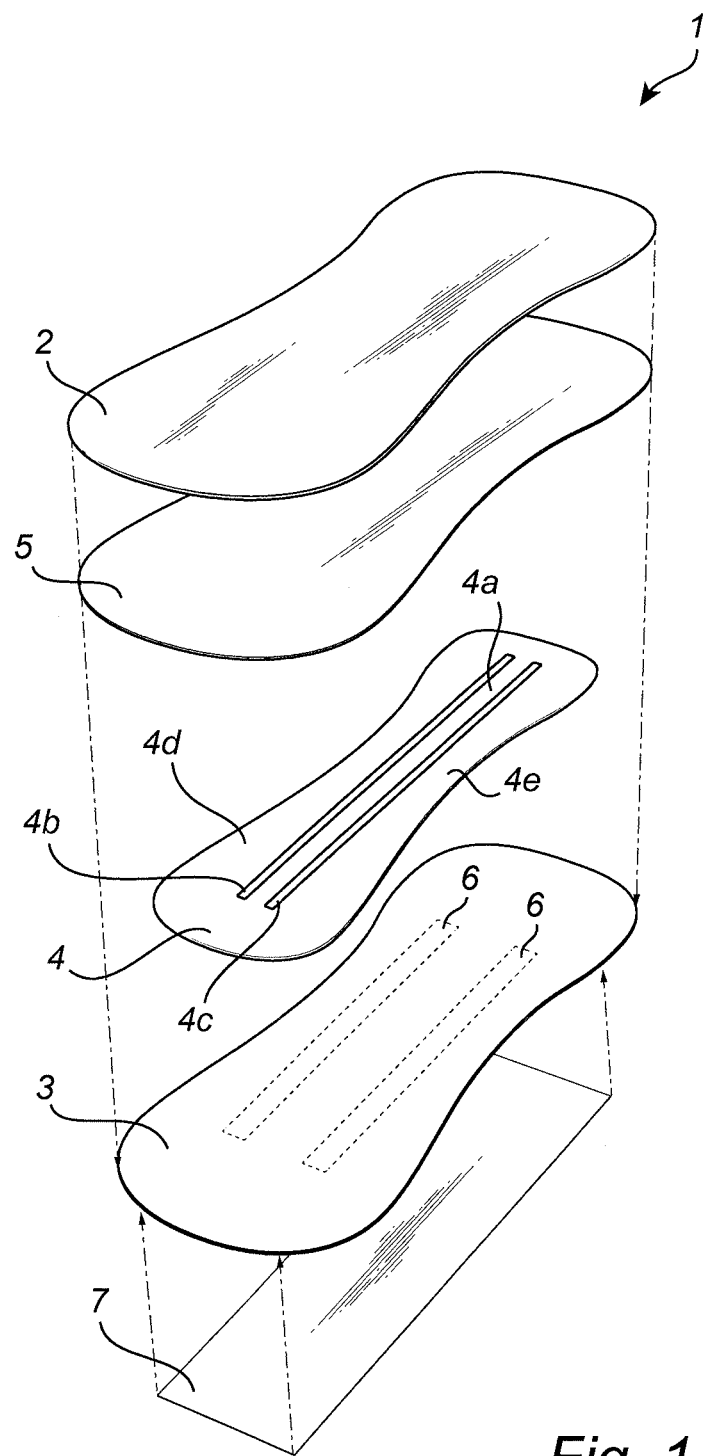
FIG. 1 shows an exploded view of a number of layers forming part of an absorbent article.

With initial reference to FIG. 1, there is shown an exploded view of a personal care absorbent article 1. According to an embodiment, the absorbent article 1 is an incontinence liner, i.e. an incontinence protector article which is specifically designed and optimized so as to absorb light urine leakage. This is opposed to, for example, menstrual pads which are designed for absorbing menstrual fluid, which is normally a thicker fluid than urine and which also normally comes out more slowly than urine. In order to provide an incontinence protector article without problem with liquid leakage, incontinence protector articles normally has an acquisition layer above the absorbent core.

However, it is to be understood that the principles of the present invention are equally applicable to any type of hygienic absorbent article. Such articles include various types of incontinence liners and pads, and also sanitary napkins, menstrual pads, panty liners or similar products which are worn inside a supporting panty. Such articles also include baby diapers, pant diapers, training pants, belted diapers or similar disposable absorbent garments.

FIG. 1 shows an incontinence liner 1 with certain layers which together form the complete liner 1. More precisely, the incontinence liner 1 includes a fluid permeable topsheet 2 and a fluid impermeable backsheet 3. The liner 1 also includes an absorbent core 4 which is sandwiched between the topsheet 2 and the backsheet 3. The topsheet 2 is arranged at the surface, i.e. the side facing the wearer, of the incontinence liner 1. The backsheet 3 is arranged at the underside of the liner 1, i.e. facing an undergarment of the wearer. Furthermore, the topsheet 2 and the backsheet 3 extend together laterally outside of the absorbent core 4 along the whole circumference of the absorbent core 4. The topsheet 2, backsheet 3 and the absorbent core 4 may be formed from any material suitable for the particular purpose, as discussed in further detail below.

Furthermore, an acquisition layer 5 (a high-loft layer) is situated between the topsheet 2 and the absorbent core 4. The acquisition layer 5 functions as an admission and transport layer which is arranged on top of the absorbent core 4 and which is especially suitable for use in an absorbent article in the form of an incontinence liner or incontinence pad. This is due to the fact that incontinence liners or incontinence pads may be used in situations where there is a discharge of a relatively high volume of fluid in a relatively short time.

The components in the liner 1 may be connected to each other by conventional means such as by means of an adhesive, heat bonding or ultrasonic bonding.

The various layers 2, 3, 4, 5 which form part of the absorbent article 1 will now be described more in detail, with reference primarily to FIGS. 1 and 2.

According to an embodiment, topsheet 2 is formed by a fluid permeable nonwoven fabric or film which is made of thermoplastic synthetic fibers. The topsheet 2 is sufficiently fluid permeable to allow discharged body fluids such as urine to penetrate through the thickness of the topsheet 2 and then reach the acquisition layer 5 and the absorbent core 4 so as to be absorbed. Also, the topsheet 2 is manufactured from a material which is compliant and soft-feeling to the skin of the wearer.

According to further embodiments, the topsheet may be manufactured from various web materials such as woven and nonwoven webs and films, foams, or combinations of the above-mentioned materials. The nonwoven materials to be used for the topsheet 2 may be for example spunbond nonwoven, carded resin bonded materials, carded through-air bonded materials, hydroentangled materials or carded thermobonded materials.

According to further embodiments, the topsheet 2 may be perforated, i.e. may be provided with fluid permeable apertures, and may optionally also have elastic properties which allows it to be stretched in any direction. Furthermore, the topsheet 2 extends across generally the entire absorbent article 1. Also, the topsheet 2 may be a single layer, or a combination of two or more layers.

Furthermore, the backsheet 3 is according to an embodiment constituted by a fluid-impermeable and breathable film of polyethylene. According to various embodiments, the materials which can be used for manufacturing the backsheet 3 include thin and flexible fluid impermeable plastic films, or fluid impermeable nonwoven materials, fluid impermeable foams and fluid impermeable laminates.

According to the embodiment shown in the drawings, the backsheet 3 is formed by a single layer, but can alternatively be formed by a multi-layered structure, i.e. a laminate, wherein at least one layer is fluid impermeable. Furthermore, the backsheet 3 can optionally be elastic in either direction. Also, backsheet materials that are not fully fluid impermeable but only resistant to fluid penetration may be used, particularly in cases where relatively small amounts of urine are expected to be absorbed by the incontinence liner 1. According to further embodiments, the backsheet 3 may be breathable, implying that air and vapor may pass through the backsheet. Furthermore, the backsheet 3 may optionally have an outer, garment-facing surface of a textile material such as nonwoven.

Figure 3:
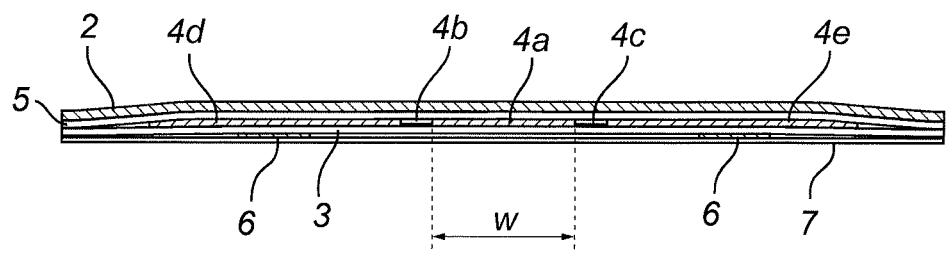
FIG. 3 shows a cross-section through the absorbent article in FIG. 2, as taken along the line III-III in FIG. 2.

As indicated in FIGS. 1 and 3, the rear side of the backsheet 3 is provided with fastening means in the form of adhesive sections 6 (shown with broken lines in FIG. 1) which are covered with a release paper layer 7 when the incontinence liner 1 is in its non-used condition. When the liner 1 is to be used, the release paper layer 7 is removed by the user so that the liner 1 can be fastened to an undergarment.

Furthermore, according to the embodiment shown in the drawings, the incontinence liner 1 includes an absorbent core 4 which is formed by a single layer including fibres of cellulosic fluff pulp and superabsorbent particles.

Furthermore, according to an embodiment, the incontinence liner 1 includes an absorbent core 4 which consists of a mixture of cellulosic fluff pulp and a suitable amount of superabsorbent particles. Such superabsorbent material is well known in the field of absorbent articles, and is constituted by a water-swellable and water-insoluble material which is capable of absorbing large quantities of fluid upon formation of a hydrogel. Normal superabsorbent materials are capable of absorbing fluids of at least 10 times its own weight. According to an embodiment, the amount of said superabsorbent particles corresponds to an amount within the interval 25-55%, 35-50%, or 37-45%, of the total weight of the absorbent core 4.

The superabsorbents are mixed with cellulose fluff pulp so as to form the absorbent core 4. The absorbent core 4 may further incorporate components for improving the properties of the absorbent core. Some examples of such components are binder fibers, fluid-dispersing materials, fluid acquisition materials, etc. as known in the art. In particular embodiments, the mixture of cellulose fluff pulp and superabsorbent articles is homogeneously mixed throughout the entire absorbent core 4.

As mentioned above, the incontinence liner 1 also includes an acquisition layer 5 which functions as a liquid inlet layer and suitably may be made from synthetic fibers such as polyester or polypropylene and can suitably be manufactured by through-air bonding. According to an embodiment, the acquisition layer 5 is constituted by a 50 gsm through air bonded carded nonwoven material. In a particular embodiment, the acquisition layer 5 is laid directly on top of the absorbent core 4. The acquisition layer 5 is adapted to rapidly acquire and distribute gushes of liquid which may be quickly introduced into the absorbent core 4.

According to further embodiments, the absorbent core 1 may be a homogeneous structure or may be a layered structure with laminates of the same or different materials.

Figure 2:
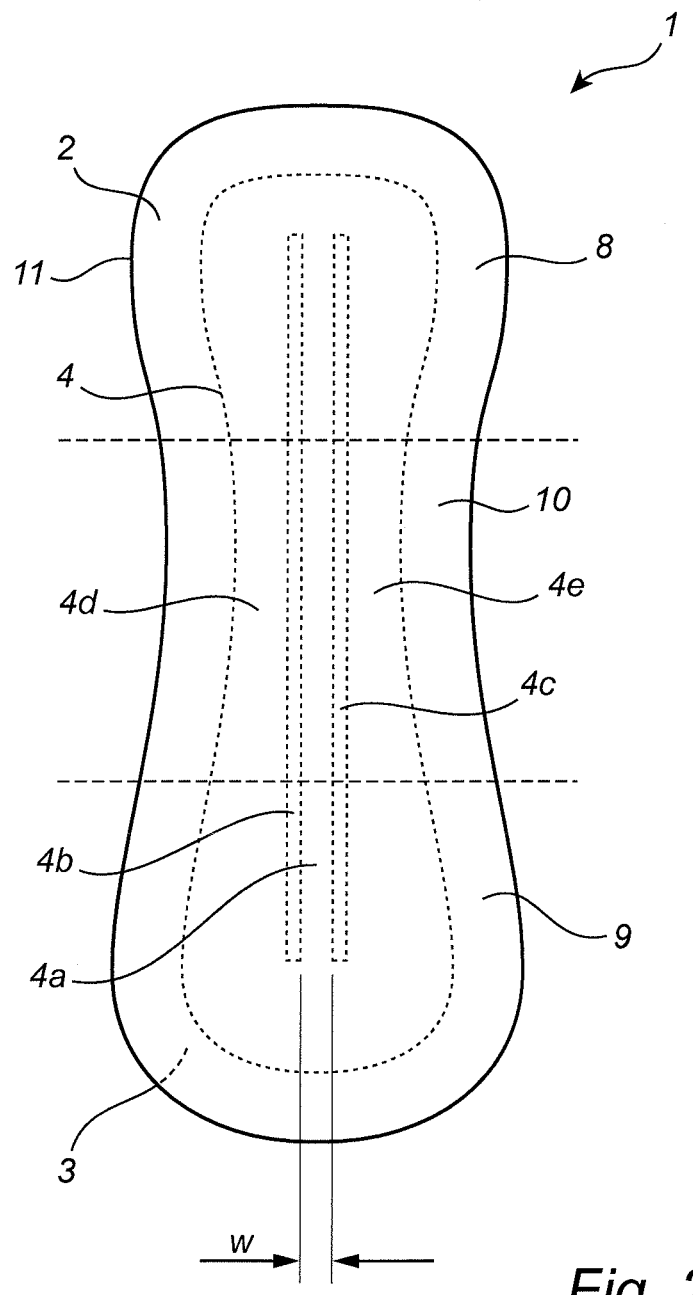
FIG. 2 shows a view of the absorbent article from the side which will be facing a user's undergarment when it is being worn.

FIG. 2 shows a view from the side of the incontinence liner 1 that is intended to be facing towards a wearer's body when the incontinence liner 1 is being worn. It can be seen from FIG. 2 that the incontinence liner 1 according to the embodiment has an elongate and generally rectangular shape including a front section 8, a rear section 9 and a crotch section 10 between the front section 8 and the rear section 9. The word "generally" in this context means that, for instance, the corners of the incontinence protector 1 may be rounded as shown in FIGS. 1 and 2. Furthermore, as shown in FIG. 2, the crotch section 10 defines a waist of the liner 1, i.e. a section of the liner 1 which has slightly less width than the width of the front section 8 and the rear section 9. Also, the crotch section 10 constitutes the main acquisition area for body fluid that reaches the liner 1.

Furthermore, the topsheet 2 and the backsheet 3 are connected to each other in an edge joint 11 around the periphery of the absorbent core 4. Also, the absorbent core 4 is of a size having an area which is slightly smaller than the area of the topsheet 2 and the backsheet 3.

The shape of the incontinence liner 1 as shown in FIGS. 1 and 2 should not be considered limiting to the invention. Accordingly, any other suitable shape may be used, such as hourglass shape, trapezoidal shape, triangular shape an oval shape. The shape of the article may be symmetrical about a transverse centre line through the article, as shown in FIG. 2, or may be asymmetrical with end portions having differing shapes and/or differing sizes. Also. the rear section 9 is intended to be orientated rearwards during use of the liner 1, whereas the front section 8 is intended to be facing forwards towards the abdomen of the wearer during use.

According to an embodiment which is shown in FIGS. 2 and 3, the absorbent core 4 is formed with a central region 4a, which is a generally longitudinally extending area situated between a first channel region 4b and a second channel region 4c. Furthermore, a first side region 4d and a second side region 4e are also defined as longitudinally extending regions on the outside of the first channel region 4b and the second channel region 4c, respectively. According to the embodiment, the two channel regions 4b, 4c are in the form of relatively thin lines along the longitudinal direction of the absorbent core 4 and which are designed in a particular manner, as will be described below.

According to the embodiment shown in the drawings, the channel regions 4b, 4c are defined by two generally straight lines, but according to alternative embodiments, may also be of curved shape or other suitable geometry.

In summary, the absorbent article 1 according to the disclosed embodiment has a longitudinal direction, a transverse direction and a thickness direction, and includes a fluid permeable topsheet 2, a fluid impermeable backsheet 3 and an absorbent core 4 enclosed between the topsheet 2 and the backsheet 3. Furthermore, the absorbent core 4 has two longitudinally extending side regions 4d, 4e and a longitudinally extending central region 4a between the side regions 4d, 4e. Also, the central region 4a and the side regions 4d, 4e are spaced apart in the transversal direction by longitudinally extending channel regions 4b, 4c.

Figure 4:
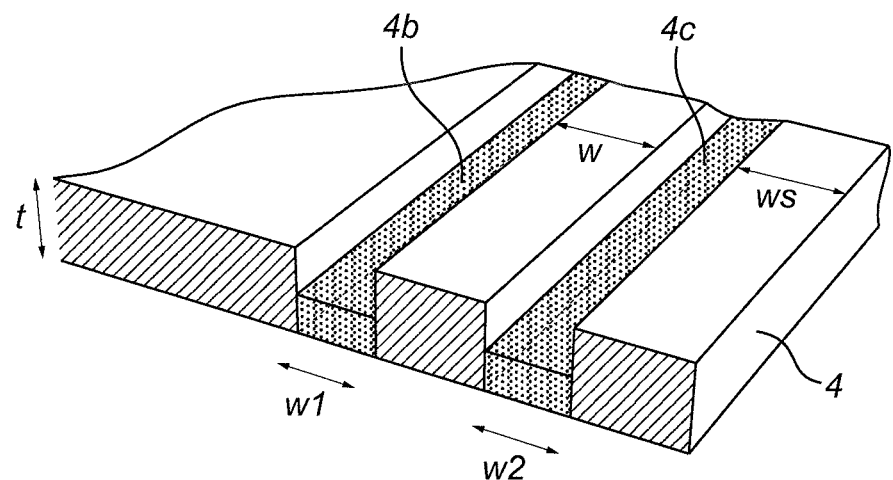
FIG. 4 is an enlarged part of the cross-section through the absorbent core as shown in FIG. 3.

According to an embodiment, and as shown in particular in FIG. 4, the channel regions 4b, 4c are formed with less material (i.e. cellulose fluff pulp, optionally mixed with superabsorbents) than the side regions 4d, 4e and the central region 4 a. More precisely, the channel regions 4b, 4c are filled with less material than the remaining part of the core 4, which is implemented by means of a special manufacturing process which will be described in greater detail below. This means that the channel regions 4b, 4c are of less overall (or average) basis weight as compared with the side regions 4d, 4e, since there is less material in said channel regions 4b, 4c. It could be said that the channel regions 4b, 4c are in the form of light basis weight areas, i.e. areas or sections of the absorbent core 4 being formed of material with a relatively low basis weight as regarded relative to the remaining areas of the absorbent core 4. This means that the material of the absorbent core 4 is of the same type both in the channel regions 4b, 4c and the remaining parts of the absorbent core 4, but there is however less material per square area in the channel regions 4b, 4c as compared to the other areas of the core 4. This also means that the channel regions 4b, 4c define regions with less basis weight than the remaining part of the absorbent core 4, i.e. a lower value corresponding to grams of material per square area (gsm), than the remaining parts of the absorbent core 4.

According to an embodiment, a suitable ratio of the basis weight between the channel regions 4b, 4c and the remaining part of the absorbent core 4 is approximately 1:2.

The purpose of the channel regions 4b, 4c is to contribute to an increase of the pliability of the absorbent core 4 and the ability for the absorbent article 1 to flex lengthwise. This is an important advantage of embodiments of the invention. Also, according to the shown embodiment, the width w of the central region 4a in the transversal direction is less than the width $w_s$ of each of the side regions 4d, 4e in the transversal direction, at least in the front- and rear section.

With reference to FIG. 4, it is noted that the width $w_1$ and $w_2$, respectively, of the two channel regions 4b, 4c is approximately 2-3 millimeters. The width w of the central region 4a is 9 mm. However, variations may occur depending on the design of the absorbent article 1 and the invention is not limited to the above-mentioned dimensions only.

Furthermore, the width $w_1$, $w_2$ of each channel region 4b, 4c is less than 0.4 times the width $w_s$ of a corresponding side region 4d, 4e. Also, the width $w_1$, $w_2$ of each channel region 4b, 4c is less than 0.1 times the width of the absorbent core 4 at its most narrow section, i.e. the crotch section 10.

Furthermore, with reference to FIG. 2, the channel regions 4b, 4c are of a length that is slightly shorter than the absorbent core 4 seen in the longitudinal direction. However, according to an alternative embodiment, the channel regions 4b, 4c may extend all the way along the absorbent core 4, so that the channel regions 4b, 4c extend along the entire length of the absorbent core.

As mentioned above, and as shown in FIGS. 1 and 3, the incontinence liner 1 also has fastening means 6 for fastening of the incontinence protector 1 inside a supporting undergarment, such as a pair of underpants (not shown in the drawings). According to an embodiment, the fastening means 6 is in the form of two longitudinally extending strips of adhesive arranged on the rear side, i.e. the garment-facing side, of the backsheet 3.

According to alternative embodiments, the incontinence liner 1 can be provided with various types of fastening means in the form of frictional fasteners, mechanical fasteners such as the hook-and-loop fastener type or combinations of different types of fasteners, as known in the art.

Furthermore, in FIGS. 1 and 2 there is indicated that the fastening means 6 is covered by a releasable protective layer 7. This protective layer may be a siliconized paper, a nonwoven or any other releasable material as is known in the art.

Figure 5:
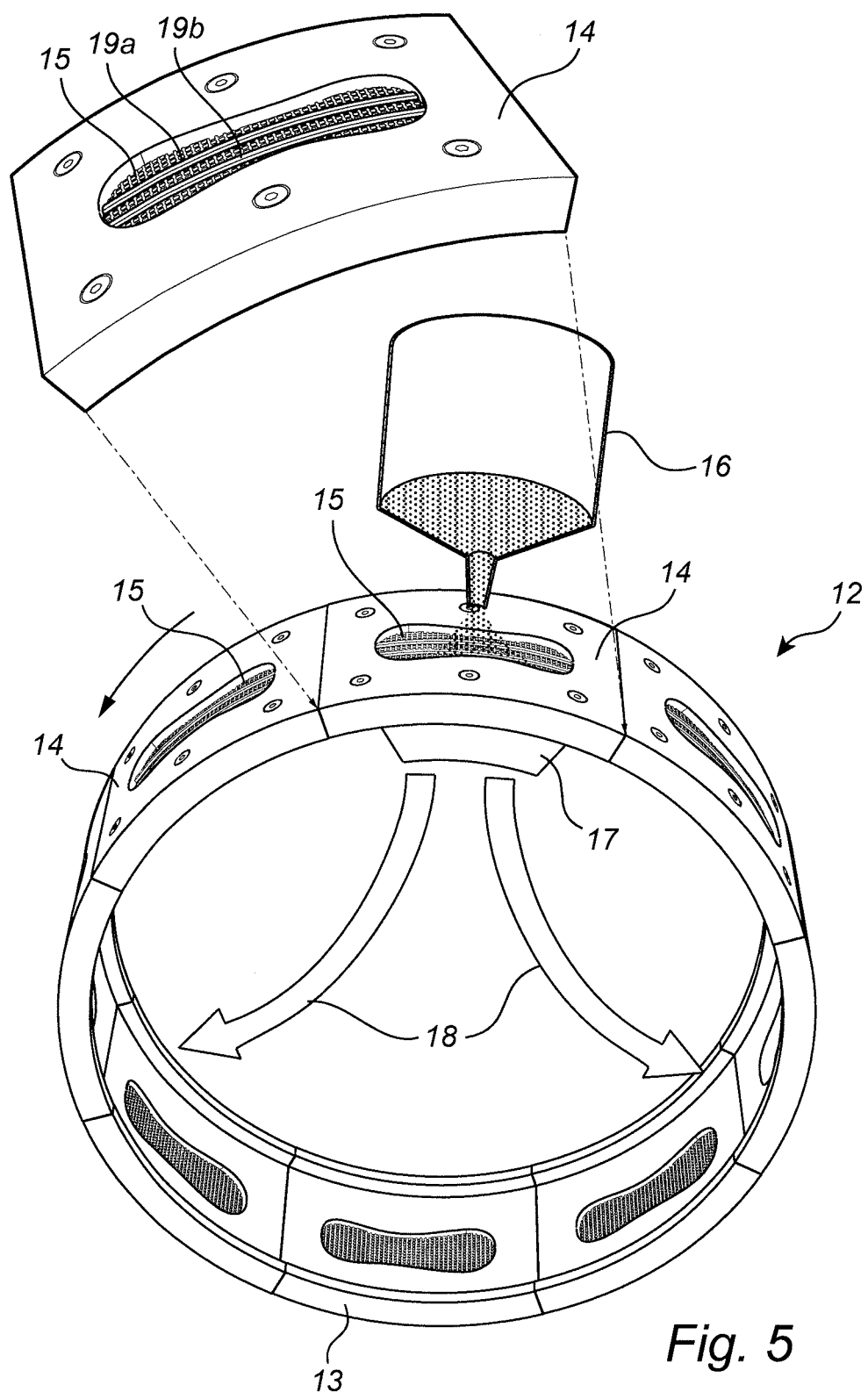
FIG. 5 shows a simplified perspective view of an arrangement for manufacturing the absorbent core.

FIG. 5 shows an arrangement for manufacturing an absorbent core 4 of the type as mentioned as mentioned above. This arrangement is based on a core forming drum 12 which includes a rotating cylinder 13. A number of core molds 14 are arranged along the circumference of the cylinder 13. Each core mold 14 is formed with an internal recess having the form of the finished absorbent core 4 and also has a screen or mesh 15 at its bottom. A supply 16 of the above-mentioned material for the absorbent core 4 (i.e. fibres of cellulosic fluff pulp, optionally mixed with superabsorbents as mentioned above) is arranged above the drum 12 in a manner so that said material fills the core molds 14 as they pass the position of the supply 16 during rotation of the cylinder 13. In order to assist this procedure, a vacuum chamber 17 including a vacuum source is arranged in the cylinder 13 so as to draw air through the core molds 14. This is symbolically indicated by means of arrows 18 in FIG. 5. In this manner, the core molds 14 can be filled with the fluff pulp material.

Furthermore, each core mold 14 is provided with two longitudinally extending narrow portions 19a, 19b which correspond to the positions of the two above-mentioned channel regions 4b, 4c forming part of the finished product.

During operation of the arrangement shown in FIG. 5, the fluff pulp material may fill each core mold 14 as it passes the supply 16. According to the embodiment, each core mold 14 has a 3D shape which is arranged so that the two light basis weight channel regions 4b, 4c are formed in each core 4. The complete absorbent core 4, with the channel regions 4b, 4c having less basis weight than the remaining parts of the core 4, is consequently formed so that when the formed core 4 exits the mold 14, it includes all necessary fluff pulp material including the low density material in the channel regions 4b, 4c.

Figure 6:
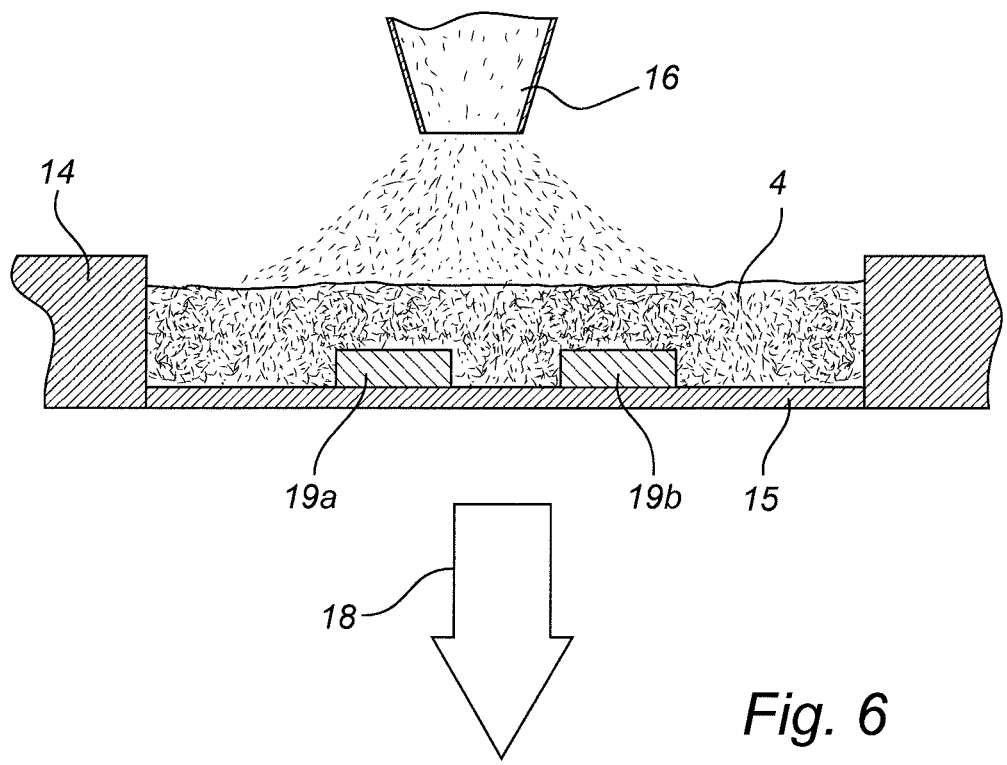
FIG. 6 shows a cross-sectional view of a core mold being used for manufacturing said absorbent core.

FIG. 6 shows a cross-sectional view of a core mold 14, so as to explain the process for manufacturing the absorbent core 4 in greater detail. As mentioned above, the core mold 14 is provided with a screen 15 through which air is drawn, as indicated with an arrow having reference numeral 18. A supply 16 of the fluff pulp material is arranged so that said material is deposited upon the screen 15, as indicated in FIG. 5.

Due to the provision of the two longitudinally extending narrow portions 19a, 19b, no air can be drawn through the core 14 just where these portions 19a, 19b are located. Also, no fluff pulp material can be deposited where the portions 19a, 19b are located. However, as the layer of fluff pulp material increases in height, fluff pulp material will be deposited on the upper side of each one of said narrow portions 19a, 19b, i.e. as the absorbent core 4 is gradually being formed.

The final form of the absorbent core 4 when it exits the core forming drum 12 will correspond to that shown in FIG. 4. The upper portions of each channel regions 4b, 4c in FIG. 4 generally correspond to the sections of the core mold 14 where the narrow portions 19a, 19b are located, i.e. these upper portions are generally free from material. In practical terms however, there may in some cases be a certain amount of material deposited on these upper parts of the channel regions 4b, 4c, which are shown as being empty in FIG. 4. For example, in some cases it can be expected that there will be a small amount of fluff pulp material deposited also in these sections. In any case, the channel regions 4b, 4c will have an overall basis weight of material which is less than the remaining parts of the absorbent core 4.

In summary, the channels 4b, 4c are formed in the core due to the specifically designed screens 15 and the narrow portions 19a, 19b, which cause relatively less core material to be deposited in the channel regions 4b, 4c as compared to the amount of material deposited in other areas of the core 4 (on a grams per square basis).

As described, each core mold 14 is formed with an internal recess having the form of the finished absorbent core 4 and the internal recess may have a thickness of for example 3-6 mm, for example 4 mm, and the longitudinally extending narrow portion 19 may have a thickness of 1-3 mm, for example 2 mm.

According to further embodiments, the process shown in FIGS. 5 and 6 for producing the absorbent cores 4 may be followed by a compression step, i.e. wherein the core 4 is pressed together in the thickness direction. This step is generally known as such, and for this reason it is not shown in detail in the drawings.

In summary, the invention is particularly intended to be used as an incontinence liner and includes an absorbent core 4 which has a central region 4a with a transversal width w which is less than the width of each of its side regions 4d, 4e, and also having channel regions 4b, 4c being of less basis weight than the side regions 4d, 4e and the central region 4a. Such an incontinence liner 1 will give advantages regarding comfort and fit during use, in particular due to the fact that the pliability of the absorbent core 4 is improved as compared with prior art solution.

The invention is not limited to the embodiment but can be varied within the scope of the appended claims. For example, the material and dimensions used for the different layers forming the absorbent article 1 can be varied as indicated above.

Test Method for Determining the Pliability of the Absorbent Article

Test Method:

Bending Mode (12-92)—test method for pliability

SUMMARY

An absorbent article according to an embodiment of the invention and as specified below presents a decrease in product stiffness by at least 25%.

Purpose and Field of Test Application:

The test method is used to define the pliability, stiffness or resistance in a product, when the product is folded or bent in a fixture designed for the purpose. The test method should describe the force that is required to shape a product to match the body after being applied to underwear.

Definition (Force):

The force is defined as the resistance that occurs when the product, which is resting on a Teflon-covered lower fixture, is folded into the fixture by the downward moving metal wires in an upper fixture.

Principle:

The product rests freely on two horizontal, parallel, Teflon-covered supports. The sample is pressed down at the centerline of the product between the two supports using a tensile tester. The maximum force is then registered. A detailed description of the test process will follow below.

Equipment:

| | |
|---|---|
| Tensile testing equipment | such as Lloyd LRX |
| Load cell | 20 N |
| Speed | 300 mm/min |
| Crosshead movement | 40 mm |
| Upper fixture | 12-92, produced by Essity Hygiene and Health AB, metal wire with a diameter of 3 mm |
| Lower fixture | 47-07, produced by Essity Hygiene and Health AB, cross-section of the supports is circular with a diameter of 10 mm and the distance between the center of the supports is 40 mm |
| Talc | such as baby powder |
| Teflon tape | PD 420, produced by Stokvis |

Sample Preparation:
1. The fixture should be fitted to the tensile tester.
2. Place product on the lower fixture. The upper fixture should be adjusted leaving a distance between the upper metal and the product. The product should have no contact with the upper fixture before start.
3. Press zero.
4. The release paper on the product should be removed before the test and the adhesive should be covered in talc to remove stickiness.

Procedure:

Place the product on the lower fixture with topsheet facing upwards. Center the product so that the upper fixture meets the product precisely in the center. Press start.

Calculation:

Maximum force should be registered. State the accuracy of the results by 1 decimal unit N.

Figure 8:
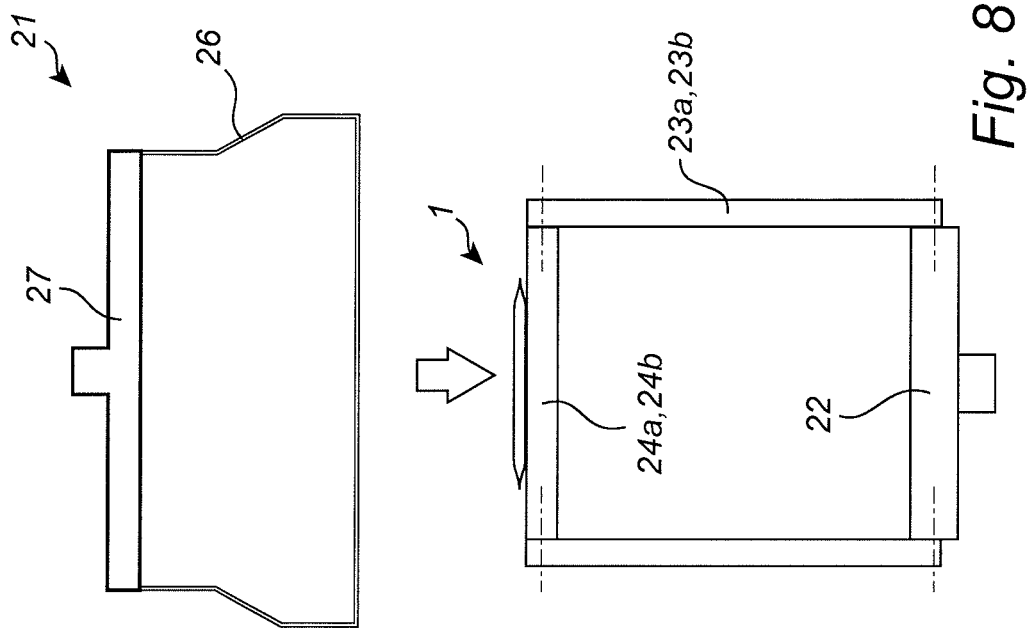
FIG. 8 is a further view of the arrangement for performing a flexural rigidity test.
Figure 7:
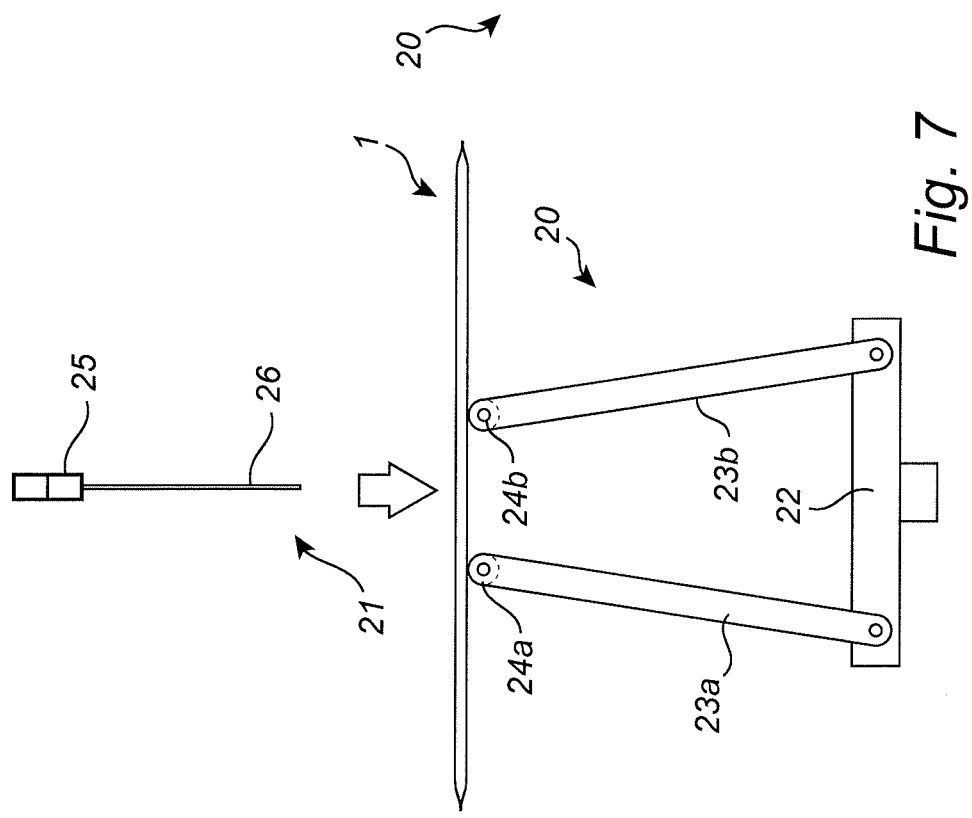
FIG. 7 is a side view of an arrangement for performing a flexural rigidity test of an absorbent article.

A more detailed description of the test method will now follow with reference to FIGS. 6 and 7. FIG. 7 is a schematic side view of the equipment used for performing the flexural rigidity test. FIG. 8 is another schematic side view of the equipment, as seen perpendicular to the view of FIG. 7.

The equipment includes a base fixture 20 for supporting an article 1 to be measured, and an upper fixture 21 to be lowered down onto the article 1 when resting on the base fixture 20. The base fixture 20 includes a base means 22 including a holder for attachment to a tensile tester. The base means 22 is provided with two support means 23a and 23b. Each support means 23a, 23b comprises two generally vertical bars and two horizontal bars 24a, 24b extending horizontally between the two generally vertical bars. The support means 23a, 23b are attached to the base means 22 in a position so as to lean somewhat towards each other. Hence, the distance between the centre of the support means means 23a, 23b at the base means 22 is about 87 mm, and the distance between the centers of the support means 23a, 23b at the horizontal bars 24a, 24b is only 40 mm. The horizontal bars 24a, 24b extend horizontally and in parallel.

The horizontal bars 24a, 24b are covered with Teflon® and have a circular cross-section with a diameter of 10 mm (including the Teflon). The surface of the horizontal bars 24a, 24b is smooth.

The upper fixture 21 includes a holder 25 for attachment to a tensile tester, and a metal wire structure 26. The metal wire structure 26 includes a horizontal portion for contacting the product 1 when lowered towards the base fixture. The horizontal portion has a length of 140 mm. At its two ends, the horizontal portion is attached to vertically extending wire portions, having a length of 50 mm. Thereafter, the wire portions continue with angled wire portions, also having a length of 50 mm, and leaning towards each other such that the upper ends of the angled wire portions are separated by a distance of 90 mm. The angled wire portions are each followed by a second horizontal wire portion having a length of 50 mm. Finally, the second horizontal wire portions are attached to the holder 25. The distance between the second horizontal wire portions at the holder 25 is thus 90 mm. The metal wire 26 has a diameter of 3 mm, and is made of a rigid and inflexible material.

The upper fixture 21 is arranged in relation to the base fixture 20 such that the metal wire structure 26 is generally parallel to the horizontal bars 24a, 24b.

For testing, the fixtures 20, 21 are mounted to the tensile tester. The upper fixture is adjusted such that the distance between the horizontal metal wire and the uppermost side of the sample when resting on the base 22 of the base fixture is about 2 mm. With this distance, the sample may easily be positioned on the base fixture. The sample shall be positioned such that the upper fixture will impact the middle of the sample.

For testing, the upper fixture is lowered towards the sample with a velocity of 200 mm/min, so as to push the product down between the horizontal supports. The test is finished when the entire product has been pushed down between the supports.

Measurement Results:

Table 1 below shows the measurement results for a conventional incontinence liner, whereas Table 2 below shows the measurement results for an incontinence liner in accordance with embodiments of the present invention. Both test series were based on a procedure involving 25 measurements.

TABLE 1

| No. | Load (N) | No. | Load (N) | No. | Load (N) | No. | Load (N) | No. | Load (N) |
|---|---|---|---|---|---|---|---|---|---|
| 1 | 1.86486 | 2 | 1.81738 | 3 | 2.39533 | 4 | 1.93933 | 5 | 1.43223 |
| 6 | 1.91535 | 7 | 2.04369 | 8 | 1.67681 | 9 | 1.53327 | 10 | 1.73858 |
| 11 | 1.78109 | 12 | 2.01489 | 13 | 2.43191 | 14 | 1.86583 | 15 | 1.64176 |
| 16 | 1.31981 | 17 | 1.59838 | 18 | 1.84993 | 19 | 1.84104 | 20 | 1.84514 |
| 21 | 1.63777 | 22 | 1.59693 | 23 | 2.28303 | 24 | 2.39323 | 25 | 1.56197 |

TABLE 2

| No. | Load (N) | No. | Load (N) | No. | Load (N) | No. | Load (N) | No. | Load (N) |
|---|---|---|---|---|---|---|---|---|---|
| 1 | 1.05162 | 2 | 1.14510 | 3 | 1.22609 | 4 | 1.22405 | 5 | 1.82324 |
| 6 | 1.26744 | 7 | 1.23330 | 8 | 1.26420 | 9 | 1.60583 | 10 | 1.26853 |
| 11 | 1.14848 | 12 | 1.52239 | 13 | 1.29964 | 14 | 1.74673 | 15 | 1.46880 |
| 16 | 2.14818 | 17 | 1.20120 | 18 | 1.44238 | 19 | 1.17635 | 20 | 1.14173 |
| 21 | 1.79068 | 22 | 1.19458 | 23 | 1.31233 | 24 | 1.35722 | 25 | 1.36632 |

CONCLUSION

In conclusion, it was noted that the mean value for the conventional incontinence liner was 1.8408 N, whereas the mean value for the incontinence liner according to an embodiment of the invention was 1.3771 N. This means that the liner according to an embodiment of the invention has a product stiffness or pliability which is 25.2% less than the conventional liner.

The invention claimed is:

1. An absorbent article having a longitudinal direction, a transverse direction and a thickness direction, and comprising a fluid permeable topsheet, a fluid impermeable backsheet and an absorbent core enclosed between the topsheet and the backsheet having, in the longitudinal direction, a front section, a rear section and a crotch section between the front section and the rear section,
    wherein the absorbent core has two longitudinally extending side regions and a longitudinally extending central region between said side regions, the central region and the side regions being spaced apart in the transversal direction by longitudinally extending channel regions,
    wherein the width of the central region in the transversal direction is less than the width of each of the side regions in the transversal direction, at least in the front section and the rear section,
    wherein the channel regions are of less basis weight than the side regions and the central region,
    wherein the channel regions and the side regions are of substantially the same thickness, and
    wherein the ratio between the basis weight of the channel regions and the basis weight of the side regions and the central region of the absorbent core is between 1:3 and 2:3.

2. An absorbent article according to claim 1, wherein the article is an incontinence liner having a single absorbent core.

3. An absorbent article according to claim 1, further comprising an acquisition layer generally covering said absorbent core.

4. An absorbent article according to claim 1, wherein the width of the central region in the transversal direction is less than the width of each of the side regions in the transversal direction also in the crotch section.

5. An absorbent article according to claim 1, wherein said absorbent core comprises superabsorbent material being generally equally distributed along said absorbent core.

6. An absorbent article according to claim 5, wherein the amount of said superabsorbent material in said absorbent core is within the interval 25-55% of the total weight of the absorbent core.

7. An absorbent article according to claim 1, wherein said article comprises a crotch region, a front region and a back region, and wherein the width of the central region is less than the width of the side regions in said crotch region.

8. An absorbent article according to claim 1, wherein said channel regions are generally parallel and straight along the longitudinal direction of the absorbent core.

9. An absorbent article according to claim 1, wherein the width of each channel region is 2-3 millimeters.

10. An absorbent article according to claim 1, wherein the width of the central region is 6-12 millimeters.

11. An absorbent article according to claim 1, wherein the width of each channel region is less than 0.4 times the width of a corresponding side region.

12. An absorbent article according to claim 1, wherein the width of each channel region is less than 0.1 times the width of the absorbent core at a most narrow region of the absorbent core.

13. An absorbent article according to claim 1, wherein the channel regions are formed in the core by deposition of core material, said deposition of core material being relatively less in the channel regions as compared to the deposition of material in other areas of the core.

14. An absorbent core for use in an absorbent article having a longitudinal direction, the absorbent core comprising two longitudinally extending side regions and a longitudinally extending central region between said side regions, the central region and the side regions being spaced apart in a transversal direction by longitudinally extending channel regions and, in the longitudinal direction, a front section, a rear section and a crotch section between the front section and the rear section, wherein the width of the central region in the transversal direction is less than the width of each of the side regions in the transversal direction, at least in the front section and the rear section, wherein the channel regions are of less basis weight than the side regions and the central region, wherein the channel regions and the side regions are of substantially the same thickness, and wherein the ratio between the basis weight of the channel regions and the basis weight of the side regions and the central region of the absorbent core is between 1:3 and 2:3.

15. An absorbent article according to claim 1, wherein the channel regions and the side regions and the central region are of substantially the same thickness throughout at least an entirety of the crotch section.

16. An absorbent article according to claim 15, wherein a density of the channel regions is lower than a density of the side regions and the central region throughout at least an entirety of the crotch section.

17. An absorbent core according to claim 14, wherein the channel regions and the side regions and the central region are of substantially the same thickness throughout at least an entirety of the crotch section.

18. An absorbent core according to claim 17, wherein a density of the channel regions is lower than a density of the side regions and the central region throughout at least an entirety of the crotch section.

* * * * *